(12) United States Patent
Johnson et al.

(10) Patent No.: US 10,569,794 B2
(45) Date of Patent: Feb. 25, 2020

(54) STABILIZER WHEEL ASSEMBLY AND METHODS OF USE

(71) Applicant: GLOBUS MEDICAL, INC., Audubon, PA (US)

(72) Inventors: Norbert Johnson, North Andover, MA (US); Timothy Moulton, Newport, RI (US); James Pelletier, Boston, MA (US); Kevin Zhang, Medford, MA (US); Jared Judson, Medford, MA (US); Gerd Schmieta, Boston, MA (US)

(73) Assignee: GLOBUS MEDICAL, INC., Audubon, PA (US)

( * ) Notice: Subject to any disclaimer, the term of this patent is extended or adjusted under 35 U.S.C. 154(b) by 0 days.

(21) Appl. No.: 16/136,815

(22) Filed: Sep. 20, 2018

(65) Prior Publication Data

US 2019/0016359 A1 Jan. 17, 2019

Related U.S. Application Data

(63) Continuation of application No. 15/681,836, filed on Aug. 21, 2017, now Pat. No. 10,106,183, which is a (Continued)

(51) Int. Cl.
*B32B 3/02* (2006.01)
*B62B 3/02* (2006.01)
(Continued)

(52) U.S. Cl.
CPC .............. *B62B 3/022* (2013.01); *A61B 34/25* (2016.02); *A61B 34/30* (2016.02); *A61B 50/13* (2016.02); *B62B 3/008* (2013.01); *B62B 3/10* (2013.01); *B62B 5/0043* (2013.01); *B62B 5/049* (2013.01); *A61G 7/0528* (2016.11);
(Continued)

(58) Field of Classification Search
CPC ........... B62B 3/022; B62B 3/008; B62B 3/10; B62B 5/049; B62B 2301/04; B60B 33/0026; B60B 33/00; B60B 33/092; B60B 33/0089; B60B 33/0042; B60K 7/0007; B60K 2007/0084; A61B 50/13; A61B 34/25; A61B 34/30; A61G 7/0528
See application file for complete search history.

(56) References Cited

U.S. PATENT DOCUMENTS 4,150,293 A 4/1979 Franke
5,184,601 A 2/1993 Putman
(Continued)

FOREIGN PATENT DOCUMENTS

DE 4321739 A1 1/1995
EP 2438897 A2 4/2012

OTHER PUBLICATIONS

US 8,231,638 B2, 07/2012, Swarup et al. (withdrawn)

*Primary Examiner* — Erez Gurari (57) ABSTRACT

Included is a stabilizer wheel assembly that may assist in stabilizing a medical device during a medical procedure. A medical device may comprise a body; and a plurality of stabilizer wheel assemblies coupled to the body, wherein the stabilizer wheel assemblies each comprise a motor assembly and a stabilization leg, wherein the motor assembly is configured to drive the stabilization leg onto a contact surface to stabilize the body.

19 Claims, 6 Drawing Sheets

Related U.S. Application Data continuation of application No. 14/881,291, filed on Oct. 13, 2015, now Pat. No. 9,771,092.

(51) Int. Cl.

| | | |
|---|---|---|
| *B62B 5/00* | (2006.01) | |
| *B62B 5/04* | (2006.01) | |
| *A61B 34/00* | (2016.01) | |
| *A61B 34/30* | (2016.01) | |
| *A61B 50/13* | (2016.01) | |
| *B62B 3/00* | (2006.01) | |
| *B62B 3/10* | (2006.01) | |
| *B60B 33/00* | (2006.01) | |
| *A61G 7/05* | (2006.01) | |

(52) U.S. Cl.
CPC ....... *B60B 33/0042* (2013.01); *B60B 33/0089* (2013.01); *B60B 33/0092* (2013.01); *B62B 2202/48* (2013.01); *B62B 2202/56* (2013.01); *B62B 2301/04* (2013.01); *B62B 2301/0467* (2013.01)

(56) References Cited

U.S. PATENT DOCUMENTS

| | | | |
|---|---|---|---|
| 5,246,010 | A | 9/1993 | Gazzara et al. |
| 5,354,314 | A | 10/1994 | Hardy et al. |
| 5,397,323 | A | 3/1995 | Taylor et al. |
| 5,598,453 | A | 1/1997 | Baba et al. |
| 5,772,594 | A | 6/1998 | Barrick |
| 5,791,908 | A | 8/1998 | Gillio |
| 5,794,639 | A | 8/1998 | Enbinder |
| 5,820,559 | A | 10/1998 | Ng et al. |
| 5,825,982 | A | 10/1998 | Wright et al. |
| 5,887,121 | A | 3/1999 | Funda et al. |
| 5,911,449 | A | 6/1999 | Daniele et al. |
| 5,951,475 | A | 9/1999 | Gueziec et al. |
| 5,987,960 | A | 11/1999 | Messner et al. |
| 6,012,216 | A | 1/2000 | Esteves et al. |
| 6,031,888 | A | 2/2000 | Ivan et al. |
| 6,033,415 | A | 3/2000 | Mittelstadt et al. |
| 6,080,181 | A | 6/2000 | Jensen et al. |
| 6,106,511 | A | 8/2000 | Jensen |
| 6,122,541 | A | 9/2000 | Cosman et al. |
| 6,144,875 | A | 11/2000 | Schweikard et al. |
| 6,157,853 | A | 12/2000 | Blume et al. |
| 6,167,145 | A | 12/2000 | Foley et al. |
| 6,167,292 | A | 12/2000 | Badano et al. |
| 6,201,984 | B1 | 3/2001 | Funda et al. |
| 6,203,196 | B1 | 3/2001 | Meyer et al. |
| 6,205,411 | B1 | 3/2001 | DiGioia, III et al. |
| 6,212,419 | B1 | 4/2001 | Blume et al. |
| 6,231,565 | B1 | 5/2001 | Tovey et al. |
| 6,236,875 | B1 | 5/2001 | Bucholz et al. |
| 6,246,900 | B1 | 6/2001 | Cosman et al. |
| 6,301,495 | B1 | 10/2001 | Gueziec et al. |
| 6,306,126 | B1 | 10/2001 | Montezuma |
| 6,312,435 | B1 | 11/2001 | Wallace et al. |
| 6,314,311 | B1 | 11/2001 | Williams et al. |
| 6,320,929 | B1 | 11/2001 | Von Der Haar |
| 6,322,567 | B1 | 11/2001 | Mittelstadt et al. |
| 6,325,808 | B1 | 12/2001 | Bernard et al. |
| 6,340,363 | B1 | 1/2002 | Bolger et al. |
| 6,377,011 | B1 | 4/2002 | Ben-Ur |
| 6,379,302 | B1 | 4/2002 | Kessman et al. |
| 6,402,762 | B2 | 6/2002 | Hunter et al. |
| 6,424,885 | B1 | 7/2002 | Niemeyer et al. |
| 6,447,503 | B1 | 9/2002 | Wynne et al. |
| 6,451,027 | B1 | 9/2002 | Cooper et al. |
| 6,477,400 | B1 | 11/2002 | Barrick |
| 6,484,049 | B1 | 11/2002 | Seeley et al. |
| 6,487,267 | B1 | 11/2002 | Wolter |
| 6,490,467 | B1 | 12/2002 | Bucholz et al. |
| 6,490,475 | B1 | 12/2002 | Seeley et al. |
| 6,499,488 | B1 | 12/2002 | Hunter et al. |
| 6,501,981 | B1 | 12/2002 | Schweikard et al. |
| 6,507,751 | B2 | 1/2003 | Blume et al. |
| 6,535,756 | B1 | 3/2003 | Simon et al. |
| 6,560,354 | B1 | 5/2003 | Maurer, Jr. et al. |
| 6,565,554 | B1 | 5/2003 | Niemeyer |
| 6,587,750 | B2 | 7/2003 | Gerbi et al. |
| 6,614,453 | B1 | 9/2003 | Suh et al. |
| 6,614,871 | B1 | 9/2003 | Kobiki et al. |
| 6,619,840 | B2 | 9/2003 | Rasche et al. |
| 6,636,757 | B1 | 10/2003 | Jascob et al. |
| 6,645,196 | B1 | 11/2003 | Nixon et al. |
| 6,666,579 | B2 | 12/2003 | Jensen |
| 6,669,635 | B2 | 12/2003 | Kessman et al. |
| 6,701,173 | B2 | 3/2004 | Nowinski et al. |
| 6,757,068 | B2 | 6/2004 | Foxlin |
| 6,782,287 | B2 | 8/2004 | Grzeszczuk et al. |
| 6,783,524 | B2 | 8/2004 | Anderson et al. |
| 6,786,896 | B1 | 9/2004 | Madhani et al. |
| 6,788,018 | B1 | 9/2004 | Blumenkranz |
| 6,804,581 | B2 | 10/2004 | Wang et al. |
| 6,823,207 | B1 | 11/2004 | Jensen et al. |
| 6,827,351 | B2 | 12/2004 | Graziani et al. |
| 6,837,892 | B2 | 1/2005 | Shoham |
| 6,839,612 | B2 | 1/2005 | Sanchez et al. |
| 6,856,826 | B2 | 2/2005 | Seeley et al. |
| 6,856,827 | B2 | 2/2005 | Seeley et al. |
| 6,879,880 | B2 | 4/2005 | Nowlin et al. |
| 6,892,090 | B2 | 5/2005 | Verard et al. |
| 6,920,347 | B2 | 7/2005 | Simon et al. |
| 6,922,632 | B2 | 7/2005 | Foxlin |
| 6,968,224 | B2 | 11/2005 | Kessman et al. |
| 6,978,166 | B2 | 12/2005 | Foley et al. |
| 6,988,009 | B2 | 1/2006 | Grimm et al. |
| 6,991,627 | B2 | 1/2006 | Madhani et al. |
| 6,996,487 | B2 | 2/2006 | Jutras et al. |
| 6,999,852 | B2 | 2/2006 | Green |
| 7,007,699 | B2 | 3/2006 | Martinelli et al. |
| 7,016,457 | B1 | 3/2006 | Senzig et al. |
| 7,043,961 | B2 | 5/2006 | Pandey et al. |
| 7,062,006 | B1 | 6/2006 | Pelc et al. |
| 7,063,705 | B2 | 6/2006 | Young et al. |
| 7,072,707 | B2 | 7/2006 | Galloway, Jr. et al. |
| 7,083,615 | B2 | 8/2006 | Peterson et al. |
| 7,097,640 | B2 | 8/2006 | Wang et al. |
| 7,099,428 | B2 | 8/2006 | Clinthorne et al. |
| 7,108,421 | B2 | 9/2006 | Gregerson et al. |
| 7,130,676 | B2 | 10/2006 | Barrick |
| 7,139,418 | B2 | 11/2006 | Abovitz et al. |
| 7,139,601 | B2 | 11/2006 | Bucholz et al. |
| 7,155,316 | B2 | 12/2006 | Sutherland et al. |
| 7,164,968 | B2 | 1/2007 | Treat et al. |
| 7,167,738 | B2 | 1/2007 | Schweikard et al. |
| 7,169,141 | B2 | 1/2007 | Brock et al. |
| 7,172,627 | B2 | 2/2007 | Fiere et al. |
| 7,194,120 | B2 | 3/2007 | Wicker et al. |
| 7,197,107 | B2 | 3/2007 | Arai et al. |
| 7,231,014 | B2 | 6/2007 | Levy |
| 7,231,063 | B2 | 6/2007 | Naimark et al. |
| 7,239,940 | B2 | 7/2007 | Wang et al. |
| 7,248,914 | B2 | 7/2007 | Hastings et al. |
| 7,301,648 | B2 | 11/2007 | Foxlin |
| 7,302,288 | B1 | 11/2007 | Schellenberg |
| 7,313,430 | B2 | 12/2007 | Urquhart et al. |
| 7,318,805 | B2 | 1/2008 | Schweikard et al. |
| 7,318,827 | B2 | 1/2008 | Leitner et al. |
| 7,319,897 | B2 | 1/2008 | Leitner et al. |
| 7,324,623 | B2 | 1/2008 | Heuscher et al. |
| 7,327,865 | B2 | 2/2008 | Fu et al. |
| 7,331,967 | B2 | 2/2008 | Lee et al. |
| 7,333,642 | B2 | 2/2008 | Green |
| 7,339,341 | B2 | 3/2008 | Oleynikov et al. |
| 7,366,562 | B2 | 4/2008 | Dukesherer et al. |
| 7,379,790 | B2 | 5/2008 | Toth et al. |
| 7,386,365 | B2 | 6/2008 | Nixon |
| 7,422,592 | B2 | 9/2008 | Morley et al. |
| 7,435,216 | B2 | 10/2008 | Kwon et al. |
| 7,440,793 | B2 | 10/2008 | Chauhan et al. |
| 7,460,637 | B2 | 12/2008 | Clinthorne et al. |

(56) References Cited

U.S. PATENT DOCUMENTS

| | | |
|---|---|---|
| 7,466,303 B2 | 12/2008 | Yi et al. |
| 7,493,153 B2 | 2/2009 | Ahmed et al. |
| 7,505,617 B2 | 3/2009 | Fu et al. |
| 7,533,892 B2 | 5/2009 | Schena et al. |
| 7,542,791 B2 | 6/2009 | Mire et al. |
| 7,555,331 B2 | 6/2009 | Viswanathan |
| 7,567,834 B2 | 7/2009 | Clayton et al. |
| 7,594,912 B2 | 9/2009 | Cooper et al. |
| 7,606,613 B2 | 10/2009 | Simon et al. |
| 7,607,440 B2 | 10/2009 | Coste-Maniere et al. |
| 7,623,902 B2 | 11/2009 | Pacheco |
| 7,630,752 B2 | 12/2009 | Viswanathan |
| 7,630,753 B2 | 12/2009 | Simon et al. |
| 7,643,862 B2 | 1/2010 | Schoenefeld |
| 7,660,623 B2 | 2/2010 | Hunter et al. |
| 7,661,881 B2 | 2/2010 | Gregerson et al. |
| 7,683,331 B2 | 3/2010 | Chang |
| 7,683,332 B2 | 3/2010 | Chang |
| 7,689,320 B2 | 3/2010 | Prisco et al. |
| 7,691,098 B2 | 4/2010 | Wallace et al. |
| 7,702,379 B2 | 4/2010 | Avinash et al. |
| 7,702,477 B2 | 4/2010 | Tuemmler et al. |
| 7,711,083 B2 | 5/2010 | Heigl et al. |
| 7,711,406 B2 | 5/2010 | Kuhn et al. |
| 7,720,523 B2 | 5/2010 | Omernick et al. |
| 7,725,253 B2 | 5/2010 | Foxlin |
| 7,726,171 B2 | 6/2010 | Langlotz et al. |
| 7,742,801 B2 | 6/2010 | Neubauer et al. |
| 7,751,865 B2 | 7/2010 | Jascob et al. |
| 7,760,849 B2 | 7/2010 | Zhang |
| 7,762,825 B2 | 7/2010 | Burbank et al. |
| 7,763,015 B2 | 7/2010 | Cooper et al. |
| 7,787,699 B2 | 8/2010 | Mahesh et al. |
| 7,796,728 B2 | 9/2010 | Bergfjord |
| 7,813,838 B2 | 10/2010 | Sommer |
| 7,818,044 B2 | 10/2010 | Dukesherer et al. |
| 7,819,859 B2 | 10/2010 | Prisco et al. |
| 7,824,401 B2 | 11/2010 | Manzo et al. |
| 7,831,294 B2 | 11/2010 | Viswanathan |
| 7,834,484 B2 | 11/2010 | Sartor |
| 7,835,557 B2 | 11/2010 | Kendrick et al. |
| 7,835,778 B2 | 11/2010 | Foley et al. |
| 7,835,784 B2 | 11/2010 | Mire et al. |
| 7,840,253 B2 | 11/2010 | Tremblay et al. |
| 7,840,256 B2 | 11/2010 | Lakin et al. |
| 7,843,158 B2 | 11/2010 | Prisco |
| 7,844,320 B2 | 11/2010 | Shahidi |
| 7,853,305 B2 | 12/2010 | Simon et al. |
| 7,853,313 B2 | 12/2010 | Thompson |
| 7,865,269 B2 | 1/2011 | Prisco et al. |
| D631,966 S | 2/2011 | Perloff et al. |
| 7,879,045 B2 | 2/2011 | Gielen et al. |
| 7,881,767 B2 | 2/2011 | Strommer et al. |
| 7,881,770 B2 | 2/2011 | Melkent et al. |
| 7,886,743 B2 | 2/2011 | Cooper et al. |
| RE42,194 E | 3/2011 | Foley et al. |
| RE42,226 E | 3/2011 | Foley et al. |
| 7,900,524 B2 | 3/2011 | Calloway et al. |
| 7,907,166 B2 | 3/2011 | Lamprecht et al. |
| 7,909,122 B2 | 3/2011 | Schena et al. |
| 7,925,653 B2 | 4/2011 | Saptharishi |
| 7,930,065 B2 | 4/2011 | Larkin et al. |
| 7,935,130 B2 | 5/2011 | Williams |
| 7,940,999 B2 | 5/2011 | Liao et al. |
| 7,945,012 B2 | 5/2011 | Ye et al. |
| 7,945,021 B2 | 5/2011 | Shapiro et al. |
| 7,953,470 B2 | 5/2011 | Vetter et al. |
| 7,954,397 B2 | 6/2011 | Choi et al. |
| 7,971,341 B2 | 7/2011 | Dukesherer et al. |
| 7,974,674 B2 | 7/2011 | Hauck et al. |
| 7,974,677 B2 | 7/2011 | Mire et al. |
| 7,974,681 B2 | 7/2011 | Wallace et al. |
| 7,979,157 B2 | 7/2011 | Anvari |
| 7,983,733 B2 | 7/2011 | Viswanathan |
| 7,988,215 B2 | 8/2011 | Seibold |
| 7,996,110 B2 | 8/2011 | Lipow et al. |
| 8,004,121 B2 | 8/2011 | Sartor |
| 8,004,229 B2 | 8/2011 | Nowlin et al. |
| 8,010,177 B2 | 8/2011 | Csavoy et al. |
| 8,019,045 B2 | 9/2011 | Kato |
| 8,021,310 B2 | 9/2011 | Sanborn et al. |
| 8,035,685 B2 | 10/2011 | Jensen |
| 8,046,054 B2 | 10/2011 | Kim et al. |
| 8,046,057 B2 | 10/2011 | Clarke |
| 8,052,688 B2 | 11/2011 | Wolf, II |
| 8,054,184 B2 | 11/2011 | Cline et al. |
| 8,054,752 B2 | 11/2011 | Druke et al. |
| 8,057,397 B2 | 11/2011 | Li et al. |
| 8,057,407 B2 | 11/2011 | Martinelli et al. |
| 8,062,288 B2 | 11/2011 | Cooper et al. |
| 8,062,375 B2 | 11/2011 | Glerum et al. |
| 8,066,524 B2 | 11/2011 | Burbank et al. |
| 8,073,335 B2 | 12/2011 | Labonville et al. |
| 8,079,950 B2 | 12/2011 | Stern et al. |
| 8,086,299 B2 | 12/2011 | Adler et al. |
| 8,092,370 B2 | 1/2012 | Roberts et al. |
| 8,098,914 B2 | 1/2012 | Liao et al. |
| 8,100,950 B2 | 1/2012 | St. Clair et al. |
| 8,105,320 B2 | 1/2012 | Manzo |
| 8,108,025 B2 | 1/2012 | Csavoy et al. |
| 8,109,877 B2 | 2/2012 | Moctezuma De La Barrera et al. |
| 8,112,292 B2 | 2/2012 | Simon |
| 8,116,430 B1 | 2/2012 | Shapiro et al. |
| 8,120,301 B2 | 2/2012 | Goldberg et al. |
| 8,121,249 B2 | 2/2012 | Wang et al. |
| 8,123,675 B2 | 2/2012 | Funda et al. |
| 8,133,229 B1 | 3/2012 | Bonutti |
| 8,142,420 B2 | 3/2012 | Schena |
| 8,147,494 B2 | 4/2012 | Leitner et al. |
| 8,150,494 B2 | 4/2012 | Simon et al. |
| 8,150,497 B2 | 4/2012 | Gielen et al. |
| 8,150,498 B2 | 4/2012 | Gielen et al. |
| 8,165,658 B2 | 4/2012 | Waynik et al. |
| 8,170,313 B2 | 5/2012 | Kendrick et al. |
| 8,179,073 B2 | 5/2012 | Farritor et al. |
| 8,182,476 B2 | 5/2012 | Julian et al. |
| 8,184,880 B2 | 5/2012 | Zhao et al. |
| 8,202,278 B2 | 6/2012 | Orban, III et al. |
| 8,208,708 B2 | 6/2012 | Homan et al. |
| 8,208,988 B2 | 6/2012 | Jensen |
| 8,219,177 B2 | 7/2012 | Smith et al. |
| 8,219,178 B2 | 7/2012 | Smith et al. |
| 8,220,468 B2 | 7/2012 | Cooper et al. |
| 8,224,024 B2 | 7/2012 | Foxlin et al. |
| 8,224,484 B2 | 7/2012 | Swarup et al. |
| 8,225,798 B2 | 7/2012 | Baldwin et al. |
| 8,228,368 B2 | 7/2012 | Zhao et al. |
| 8,231,610 B2 | 7/2012 | Jo et al. |
| 8,263,933 B2 | 7/2012 | Hartmann et al. |
| 8,239,001 B2 | 8/2012 | Verard et al. |
| 8,241,271 B2 | 8/2012 | Millman et al. |
| 8,248,413 B2 | 8/2012 | Gattani et al. |
| 8,256,319 B2 | 9/2012 | Cooper et al. |
| 8,271,069 B2 | 9/2012 | Jascob et al. |
| 8,271,130 B2 | 9/2012 | Hourtash |
| 8,281,670 B2 | 10/2012 | Larkin et al. |
| 8,282,653 B2 | 10/2012 | Nelson et al. |
| 8,301,226 B2 | 10/2012 | Csavoy et al. |
| 8,311,611 B2 | 11/2012 | Csavoy et al. |
| 8,320,991 B2 | 11/2012 | Jascob et al. |
| 8,332,012 B2 | 12/2012 | Kienzle, III |
| 8,333,755 B2 | 12/2012 | Cooper et al. |
| 8,335,552 B2 | 12/2012 | Stiles |
| 8,335,557 B2 | 12/2012 | Maschke |
| 8,348,931 B2 | 1/2013 | Cooper et al. |
| 8,353,963 B2 | 1/2013 | Glerum |
| 8,358,818 B2 | 1/2013 | Miga et al. |
| 8,359,730 B2 | 1/2013 | Burg et al. |
| 8,365,353 B2 * | 2/2013 | Block .................. B60B 33/0007 16/35 R |
| 8,374,673 B2 | 2/2013 | Adcox et al. |
| 8,374,723 B2 | 2/2013 | Zhao et al. |
| 8,379,791 B2 | 2/2013 | Forthmann et al. |
| 8,386,019 B2 | 2/2013 | Camus et al. |

(56) References Cited

U.S. PATENT DOCUMENTS

| | | |
|---|---|---|
| 8,392,022 B2 | 3/2013 | Ortmaier et al. |
| 8,394,099 B2 | 3/2013 | Patwardhan |
| 8,395,342 B2 | 3/2013 | Prisco |
| 8,398,634 B2 | 3/2013 | Manzo et al. |
| 8,400,094 B2 | 3/2013 | Schena |
| 8,414,957 B2 | 4/2013 | Enzerink et al. |
| 8,418,073 B2 | 4/2013 | Mohr et al. |
| 8,450,694 B2 | 5/2013 | Baviera et al. |
| 8,452,447 B2 | 5/2013 | Nixon |
| RE44,305 E | 6/2013 | Foley et al. |
| 8,462,911 B2 | 6/2013 | Vesel et al. |
| 8,465,476 B2 | 6/2013 | Rogers et al. |
| 8,465,771 B2 | 6/2013 | Wan et al. |
| 8,467,851 B2 | 6/2013 | Mire et al. |
| 8,467,852 B2 | 6/2013 | Csavoy et al. |
| 8,469,947 B2 | 6/2013 | Devengenzo et al. |
| RE44,392 E | 7/2013 | Hynes |
| 8,483,434 B2 | 7/2013 | Buehner et al. |
| 8,483,800 B2 | 7/2013 | Jensen et al. |
| 8,486,532 B2 | 7/2013 | Enzerink et al. |
| 8,489,235 B2 | 7/2013 | Moll et al. |
| 8,500,722 B2 | 8/2013 | Cooper |
| 8,500,728 B2 | 8/2013 | Newton et al. |
| 8,504,201 B2 | 8/2013 | Moll et al. |
| 8,506,555 B2 | 8/2013 | Ruiz Morales |
| 8,506,556 B2 | 8/2013 | Schena |
| 8,508,173 B2 | 8/2013 | Goldberg et al. |
| 8,512,318 B2 | 8/2013 | Tovey et al. |
| 8,515,576 B2 | 8/2013 | Lipow et al. |
| 8,518,120 B2 | 8/2013 | Glerum et al. |
| 8,521,331 B2 | 8/2013 | Itkowitz |
| 8,526,688 B2 | 9/2013 | Groszmann et al. |
| 8,526,700 B2 | 9/2013 | Issacs |
| 8,527,094 B2 | 9/2013 | Kumar et al. |
| 8,528,440 B2 | 9/2013 | Morley et al. |
| 8,532,741 B2 | 9/2013 | Heruth et al. |
| 8,541,970 B2 | 9/2013 | Nowlin et al. |
| 8,548,563 B2 | 10/2013 | Simon et al. |
| 8,549,732 B2 | 10/2013 | Burg et al. |
| 8,551,114 B2 | 10/2013 | Ramos de la Pena |
| 8,551,116 B2 | 10/2013 | Julian et al. |
| 8,556,807 B2 | 10/2013 | Scott et al. |
| 8,556,979 B2 | 10/2013 | Glerum et al. |
| 8,560,118 B2 | 10/2013 | Green et al. |
| 8,561,473 B2 | 10/2013 | Blumenkranz |
| 8,562,594 B2 | 10/2013 | Cooper et al. |
| 8,571,638 B2 | 10/2013 | Shoham |
| 8,571,710 B2 | 10/2013 | Coste-Maniere et al. |
| 8,573,465 B2 | 11/2013 | Shelton, IV |
| 8,574,303 B2 | 11/2013 | Sharkey et al. |
| 8,585,420 B2 | 11/2013 | Burbank et al. |
| 8,594,841 B2 | 11/2013 | Zhao et al. |
| 8,597,198 B2 | 12/2013 | Sanborn et al. |
| 8,600,478 B2 | 12/2013 | Verard et al. |
| 8,603,077 B2 | 12/2013 | Cooper et al. |
| 8,611,985 B2 | 12/2013 | Lavallee et al. |
| 8,613,230 B2 | 12/2013 | Blumenkranz et al. |
| 8,621,939 B2 | 1/2014 | Blumenkranz et al. |
| 8,624,537 B2 | 1/2014 | Nowlin et al. |
| 8,630,389 B2 | 1/2014 | Kato |
| 8,634,897 B2 | 1/2014 | Simon et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,639,000 B2 | 1/2014 | Zhao et al. |
| 8,641,726 B2 | 2/2014 | Bonutti |
| 8,644,907 B2 | 2/2014 | Hartmann et al. |
| 8,657,809 B2 | 2/2014 | Schoepp |
| 8,660,635 B2 | 2/2014 | Simon et al. |
| 8,666,544 B2 | 3/2014 | Moll et al. |
| 8,675,939 B2 | 3/2014 | Moctezuma de la Barrera |
| 8,678,647 B2 | 3/2014 | Gregerson et al. |
| 8,679,125 B2 | 3/2014 | Smith et al. |
| 8,679,183 B2 | 3/2014 | Glerum et al. |
| 8,682,413 B2 | 3/2014 | Lloyd |
| 8,684,253 B2 | 4/2014 | Giordano et al. |
| 8,685,098 B2 | 4/2014 | Glerum et al. |
| 8,693,730 B2 | 4/2014 | Umasuthan et al. |
| 8,694,075 B2 | 4/2014 | Groszmann et al. |
| 8,696,458 B2 | 4/2014 | Foxlin et al. |
| 8,700,123 B2 | 4/2014 | Okamura et al. |
| 8,706,086 B2 | 4/2014 | Glerum |
| 8,706,185 B2 | 4/2014 | Foley et al. |
| 8,706,301 B2 | 4/2014 | Zhao et al. |
| 8,717,430 B2 | 5/2014 | Simon et al. |
| 8,727,618 B2 | 5/2014 | Maschke et al. |
| 8,734,432 B2 | 5/2014 | Tuma et al. |
| 8,738,115 B2 | 5/2014 | Amberg et al. |
| 8,738,181 B2 | 5/2014 | Greer et al. |
| 8,740,882 B2 | 6/2014 | Jun et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,761,930 B2 | 6/2014 | Nixon |
| 8,764,448 B2 | 7/2014 | Yang et al. |
| 8,771,170 B2 | 7/2014 | Mesallum et al. |
| 8,781,186 B2 | 7/2014 | Clements et al. |
| 8,781,630 B2 | 7/2014 | Banks et al. |
| 8,784,385 B2 | 7/2014 | Boyden et al. |
| 8,786,241 B2 | 7/2014 | Nowlin et al. |
| 8,787,520 B2 | 7/2014 | Baba |
| 8,792,704 B2 | 7/2014 | Isaacs |
| 8,798,231 B2 | 8/2014 | Notohara et al. |
| 8,800,838 B2 | 8/2014 | Shelton, IV |
| 8,808,164 B2 | 8/2014 | Hoffman et al. |
| 8,812,077 B2 | 8/2014 | Dempsey |
| 8,814,793 B2 | 8/2014 | Brabrand |
| 8,816,628 B2 | 8/2014 | Nowlin et al. |
| 8,818,105 B2 | 8/2014 | Myronenko et al. |
| 8,820,605 B2 | 9/2014 | Shelton, IV |
| 8,821,511 B2 | 9/2014 | von Jako et al. |
| 8,823,308 B2 | 9/2014 | Nowlin et al. |
| 8,827,996 B2 | 9/2014 | Scott et al. |
| 8,828,024 B2 | 9/2014 | Farritor et al. |
| 8,830,224 B2 | 9/2014 | Zhao et al. |
| 8,834,489 B2 | 9/2014 | Cooper et al. |
| 8,834,490 B2 | 9/2014 | Bonutti |
| 8,838,270 B2 | 9/2014 | Druke et al. |
| 8,844,789 B2 | 9/2014 | Shelton, IV et al. |
| 8,855,822 B2 | 10/2014 | Bartol et al. |
| 8,858,598 B2 | 10/2014 | Seifert et al. |
| 8,860,753 B2 | 10/2014 | Bhandarkar et al. |
| 8,864,751 B2 | 10/2014 | Prisco et al. |
| 8,864,798 B2 | 10/2014 | Weiman et al. |
| 8,864,833 B2 | 10/2014 | Glerum et al. |
| 8,867,703 B2 | 10/2014 | Shapiro et al. |
| 8,870,880 B2 | 10/2014 | Himmelberger et al. |
| 8,876,866 B2 | 11/2014 | Zappacosta et al. |
| 8,880,223 B2 | 11/2014 | Raj et al. |
| 8,882,803 B2 | 11/2014 | Iott et al. |
| 8,883,210 B1 | 11/2014 | Truncale et al. |
| 8,888,821 B2 | 11/2014 | Rezach et al. |
| 8,888,853 B2 | 11/2014 | Glerum et al. |
| 8,888,854 B2 | 11/2014 | Glerum et al. |
| 8,894,652 B2 | 11/2014 | Seifert et al. |
| 8,894,688 B2 | 11/2014 | Suh |
| 8,894,691 B2 | 11/2014 | Iott et al. |
| 8,906,069 B2 | 12/2014 | Hansell et al. |
| 8,964,934 B2 | 2/2015 | Ein-Gal |
| 8,992,580 B2 | 3/2015 | Bar et al. |
| 8,996,169 B2 | 3/2015 | Lightcap et al. |
| 9,001,963 B2 | 4/2015 | Sowards-Emmerd et al. |
| 9,002,076 B2 | 4/2015 | Khadem et al. |
| 9,044,190 B2 | 6/2015 | Rubner et al. |
| 9,107,683 B2 | 8/2015 | Hourtash et al. |
| 9,125,556 B2 | 9/2015 | Zehavi et al. |
| 9,131,986 B2 | 9/2015 | Greer et al. |
| 9,215,968 B2 | 12/2015 | Schostek et al. |
| 9,308,050 B2 | 4/2016 | Kostrzewski et al. |
| 9,380,984 B2 | 7/2016 | Li et al. |
| 9,393,039 B2 | 7/2016 | Lechner et al. |
| 9,398,886 B2 | 7/2016 | Gregerson et al. |
| 9,398,890 B2 | 7/2016 | Dong et al. |
| 9,414,859 B2 | 8/2016 | Ballard et al. |

(56) References Cited

U.S. PATENT DOCUMENTS

| | | |
|---|---|---|
| 9,420,975 B2 | 8/2016 | Gutfleisch et al. |
| 9,492,235 B2 | 11/2016 | Hourtash et al. |
| 9,592,096 B2 | 3/2017 | Maillet et al. |
| 9,750,465 B2 | 9/2017 | Engel et al. |
| 9,757,203 B2 | 9/2017 | Hourtash et al. |
| 9,795,354 B2 | 10/2017 | Menegaz et al. |
| 9,814,535 B2 | 11/2017 | Bar et al. |
| 9,820,783 B2 | 11/2017 | Donner et al. |
| 9,833,265 B2 | 11/2017 | Donner et al. |
| 9,848,922 B2 | 12/2017 | Tohmeh et al. |
| 9,925,011 B2 | 3/2018 | Gombert et al. |
| 9,931,025 B1 | 4/2018 | Graetzel et al. |
| 10,034,717 B2 | 7/2018 | Miller et al. |
| 2001/0036302 A1 | 11/2001 | Miller |
| 2002/0035321 A1 | 3/2002 | Bucholz et al. |
| 2004/0068172 A1 | 4/2004 | Nowinski et al. |
| 2004/0076259 A1 | 4/2004 | Jensen et al. |
| 2005/0096502 A1 | 5/2005 | Khalili |
| 2005/0143651 A1 | 6/2005 | Verard et al. |
| 2005/0171558 A1 | 8/2005 | Abovitz et al. |
| 2006/0100610 A1 | 5/2006 | Wallace et al. |
| 2006/0173329 A1 | 8/2006 | Marquart et al. |
| 2006/0184396 A1 | 8/2006 | Dennis et al. |
| 2006/0241416 A1 | 10/2006 | Marquart et al. |
| 2006/0291612 A1 | 12/2006 | Nishide et al. |
| 2007/0015987 A1 | 1/2007 | Benlloch Baviera et al. |
| 2007/0021738 A1 | 1/2007 | Nasser et al. |
| 2007/0038059 A1 | 2/2007 | Sheffer et al. |
| 2007/0073133 A1 | 3/2007 | Schoenefeld |
| 2007/0114079 A1 | 5/2007 | Chao |
| 2007/0156121 A1 | 7/2007 | Millman et al. |
| 2007/0156157 A1 | 7/2007 | Nahum et al. |
| 2007/0167712 A1 | 7/2007 | Keglovich et al. |
| 2007/0233238 A1 | 10/2007 | Huynh et al. |
| 2008/0004523 A1 | 1/2008 | Jensen |
| 2008/0013809 A1 | 1/2008 | Zhu et al. |
| 2008/0033283 A1 | 2/2008 | Dellaca et al. |
| 2008/0046122 A1 | 2/2008 | Manzo et al. |
| 2008/0082109 A1 | 4/2008 | Moll et al. |
| 2008/0108912 A1 | 5/2008 | Node-Langlois |
| 2008/0108991 A1 | 5/2008 | von Jako |
| 2008/0109012 A1 | 5/2008 | Falco et al. |
| 2008/0144906 A1 | 6/2008 | Allred et al. |
| 2008/0161680 A1 | 7/2008 | von Jako et al. |
| 2008/0161682 A1 | 7/2008 | Kendrick et al. |
| 2008/0177203 A1 | 7/2008 | von Jako |
| 2008/0214922 A1 | 9/2008 | Hartmann et al. |
| 2008/0228068 A1 | 9/2008 | Viswanathan et al. |
| 2008/0228196 A1 | 9/2008 | Wang et al. |
| 2008/0235052 A1 | 9/2008 | Node-Langlois et al. |
| 2008/0269596 A1 | 10/2008 | Revie et al. |
| 2008/0287771 A1 | 11/2008 | Anderson |
| 2008/0287781 A1 | 11/2008 | Revie et al. |
| 2008/0300477 A1 | 12/2008 | Lloyd et al. |
| 2008/0300478 A1 | 12/2008 | Zuhars et al. |
| 2008/0302950 A1 | 12/2008 | Park et al. |
| 2008/0306490 A1 | 12/2008 | Lakin et al. |
| 2008/0319311 A1 | 12/2008 | Hamadeh |
| 2009/0012509 A1 | 1/2009 | Csavoy et al. |
| 2009/0030428 A1 | 1/2009 | Omori et al. |
| 2009/0080737 A1 | 3/2009 | Battle et al. |
| 2009/0185655 A1 | 7/2009 | Koken et al. |
| 2009/0198121 A1 | 8/2009 | Hoheisel |
| 2009/0216113 A1 | 8/2009 | Meier et al. |
| 2009/0228019 A1 | 9/2009 | Gross et al. |
| 2009/0259123 A1 | 10/2009 | Navab et al. |
| 2009/0259230 A1 | 10/2009 | Khadem et al. |
| 2009/0264899 A1 | 10/2009 | Appenrodt et al. |
| 2009/0281417 A1 | 11/2009 | Hartmann et al. |
| 2010/0022874 A1 | 1/2010 | Wang et al. |
| 2010/0039506 A1 | 2/2010 | Sarvestani et al. |
| 2010/0125286 A1 | 5/2010 | Wang et al. |
| 2010/0130986 A1 | 5/2010 | Mailloux et al. |
| 2010/0228117 A1 | 9/2010 | Hartmann |
| 2010/0228265 A1 | 9/2010 | Prisco |
| 2010/0249571 A1 | 9/2010 | Jensen et al. |
| 2010/0274120 A1 | 10/2010 | Heuscher |
| 2010/0280363 A1 | 11/2010 | Skarda et al. |
| 2010/0331858 A1 | 12/2010 | Simaan et al. |
| 2011/0022229 A1 | 1/2011 | Jang et al. |
| 2011/0077504 A1 | 3/2011 | Fischer et al. |
| 2011/0098553 A1 | 4/2011 | Robbins et al. |
| 2011/0137152 A1 | 6/2011 | Li |
| 2011/0213384 A1 | 9/2011 | Jeong |
| 2011/0224684 A1 | 9/2011 | Larkin et al. |
| 2011/0224685 A1 | 9/2011 | Larkin et al. |
| 2011/0224686 A1 | 9/2011 | Larkin et al. |
| 2011/0224687 A1 | 9/2011 | Larkin et al. |
| 2011/0224688 A1 | 9/2011 | Larkin et al. |
| 2011/0224689 A1 | 9/2011 | Larkin et al. |
| 2011/0224825 A1 | 9/2011 | Larkin et al. |
| 2011/0230967 A1 | 9/2011 | O'Halloran et al. |
| 2011/0238080 A1 | 9/2011 | Ranjit et al. |
| 2011/0276058 A1 | 11/2011 | Choi et al. |
| 2011/0282189 A1 | 11/2011 | Graumann |
| 2011/0286573 A1 | 11/2011 | Schretter et al. |
| 2011/0295062 A1 | 12/2011 | Gratacos Solsona et al. |
| 2011/0295370 A1 | 12/2011 | Suh et al. |
| 2011/0306986 A1 | 12/2011 | Lee et al. |
| 2012/0035507 A1 | 2/2012 | George et al. |
| 2012/0046668 A1 | 2/2012 | Gantes |
| 2012/0051498 A1 | 3/2012 | Koishi |
| 2012/0053597 A1 | 3/2012 | Anvari et al. |
| 2012/0059248 A1 | 3/2012 | Holsing et al. |
| 2012/0071753 A1 | 3/2012 | Hunter et al. |
| 2012/0108954 A1 | 5/2012 | Schulhauser et al. |
| 2012/0136372 A1 | 5/2012 | Amat Girbau et al. |
| 2012/0143084 A1 | 6/2012 | Shoham |
| 2012/0184839 A1 | 7/2012 | Woerlein |
| 2012/0197182 A1 | 8/2012 | Millman et al. |
| 2012/0226145 A1 | 9/2012 | Chang et al. |
| 2012/0235909 A1 | 9/2012 | Birkenbach et al. |
| 2012/0245596 A1 | 9/2012 | Meenink |
| 2012/0253332 A1 | 10/2012 | Moll |
| 2012/0253360 A1 | 10/2012 | White et al. |
| 2012/0256092 A1 | 10/2012 | Zingerman |
| 2012/0294498 A1 | 11/2012 | Popovic |
| 2012/0296203 A1 | 11/2012 | Hartmann et al. |
| 2013/0006267 A1 | 1/2013 | Odermatt et al. |
| 2013/0016889 A1 | 1/2013 | Myronenko et al. |
| 2013/0030571 A1 | 1/2013 | Ruiz Morales et al. |
| 2013/0035583 A1 | 2/2013 | Park et al. |
| 2013/0060146 A1 | 3/2013 | Yang et al. |
| 2013/0060337 A1 | 3/2013 | Petersheim et al. |
| 2013/0094742 A1 | 4/2013 | Feilkas |
| 2013/0096574 A1 | 4/2013 | Kang et al. |
| 2013/0113791 A1 | 5/2013 | Isaacs et al. |
| 2013/0116706 A1 | 5/2013 | Lee et al. |
| 2013/0131695 A1 | 5/2013 | Scarfogliero et al. |
| 2013/0144307 A1 | 6/2013 | Jeong et al. |
| 2013/0158542 A1 | 6/2013 | Manzo et al. |
| 2013/0165937 A1 | 6/2013 | Patwardhan |
| 2013/0178867 A1 | 7/2013 | Farritor et al. |
| 2013/0178868 A1 | 7/2013 | Roh |
| 2013/0178870 A1 | 7/2013 | Schena |
| 2013/0204271 A1 | 8/2013 | Brisson et al. |
| 2013/0211419 A1 | 8/2013 | Jensen |
| 2013/0211420 A1 | 8/2013 | Jensen |
| 2013/0218142 A1 | 8/2013 | Tuma et al. |
| 2013/0223702 A1 | 8/2013 | Holsing et al. |
| 2013/0225942 A1 | 8/2013 | Holsing et al. |
| 2013/0225943 A1 | 8/2013 | Holsing et al. |
| 2013/0231556 A1 | 9/2013 | Holsing et al. |
| 2013/0237995 A1 | 9/2013 | Lee et al. |
| 2013/0245375 A1 | 9/2013 | DiMaio et al. |
| 2013/0261640 A1 | 10/2013 | Kim et al. |
| 2013/0272488 A1 | 10/2013 | Bailey et al. |
| 2013/0272489 A1 | 10/2013 | Dickman et al. |
| 2013/0274761 A1 | 10/2013 | Devengenzo et al. |
| 2013/0281821 A1 | 10/2013 | Liu et al. |
| 2013/0296884 A1 | 11/2013 | Taylor et al. |
| 2013/0303887 A1 | 11/2013 | Holsing et al. |
| 2013/0307955 A1 | 11/2013 | Deitz et al. |
| 2013/0317521 A1 | 11/2013 | Choi et al. |

(56) References Cited

U.S. PATENT DOCUMENTS

| | | |
|---|---|---|
| 2013/0325033 A1 | 12/2013 | Schena et al. |
| 2013/0325035 A1 | 12/2013 | Hauck et al. |
| 2013/0331686 A1 | 12/2013 | Freysinger et al. |
| 2013/0331858 A1 | 12/2013 | Devengenzo et al. |
| 2013/0331861 A1 | 12/2013 | Yoon |
| 2013/0342578 A1 | 12/2013 | Isaacs |
| 2013/0345717 A1 | 12/2013 | Markvicka et al. |
| 2013/0345757 A1 | 12/2013 | Stad |
| 2014/0001235 A1 | 1/2014 | Shelton, IV |
| 2014/0012131 A1 | 1/2014 | Heruth et al. |
| 2014/0031664 A1 | 1/2014 | Kang et al. |
| 2014/0046128 A1 | 2/2014 | Lee et al. |
| 2014/0046132 A1 | 2/2014 | Hoeg et al. |
| 2014/0046340 A1 | 2/2014 | Wilson et al. |
| 2014/0049629 A1 | 2/2014 | Siewerdsen et al. |
| 2014/0058406 A1 | 2/2014 | Tsekos |
| 2014/0059768 A1 | 3/2014 | Lemire et al. |
| 2014/0073914 A1 | 3/2014 | Lavallee et al. |
| 2014/0080086 A1 | 3/2014 | Chen |
| 2014/0081128 A1 | 3/2014 | Verard et al. |
| 2014/0088612 A1 | 3/2014 | Bartol et al. |
| 2014/0094694 A1 | 4/2014 | Moctezuma de la Barrera |
| 2014/0094851 A1 | 4/2014 | Gordon |
| 2014/0096369 A1 | 4/2014 | Matsumoto et al. |
| 2014/0100587 A1 | 4/2014 | Farritor et al. |
| 2014/0121676 A1 | 5/2014 | Kostrzewski et al. |
| 2014/0128882 A1 | 5/2014 | Kwak et al. |
| 2014/0135796 A1 | 5/2014 | Simon et al. |
| 2014/0142591 A1 | 5/2014 | Alvarez et al. |
| 2014/0142592 A1 | 5/2014 | Moon et al. |
| 2014/0148692 A1 | 5/2014 | Hartmann et al. |
| 2014/0163581 A1 | 6/2014 | Devengenzo et al. |
| 2014/0171781 A1 | 6/2014 | Stiles |
| 2014/0171900 A1 | 6/2014 | Stiles |
| 2014/0171965 A1 | 6/2014 | Loh et al. |
| 2014/0180308 A1 | 6/2014 | von Grunberg |
| 2014/0180309 A1 | 6/2014 | Seeber et al. |
| 2014/0187915 A1 | 7/2014 | Yaroshenko et al. |
| 2014/0188132 A1 | 7/2014 | Kang |
| 2014/0194699 A1 | 7/2014 | Roh et al. |
| 2014/0130810 A1 | 8/2014 | Azizian et al. |
| 2014/0221819 A1 | 8/2014 | Sarment |
| 2014/0222023 A1 | 8/2014 | Kim et al. |
| 2014/0228631 A1 | 8/2014 | Kwak et al. |
| 2014/0234804 A1 | 8/2014 | Huang et al. |
| 2014/0243849 A1* | 8/2014 | Saglam .................. A61B 18/22 606/130 |
| 2014/0257328 A1 | 9/2014 | Kim et al. |
| 2014/0257329 A1 | 9/2014 | Jang et al. |
| 2014/0257330 A1 | 9/2014 | Choi et al. |
| 2014/0275760 A1 | 9/2014 | Lee et al. |
| 2014/0275955 A1 | 9/2014 | Crawford et al. |
| 2014/0275985 A1 | 9/2014 | Walker et al. |
| 2014/0276931 A1 | 9/2014 | Parihar et al. |
| 2014/0276940 A1 | 9/2014 | Seo |
| 2014/0276944 A1 | 9/2014 | Farritor et al. |
| 2014/0288413 A1 | 9/2014 | Hwang et al. |
| 2014/0299648 A1 | 10/2014 | Shelton, IV et al. |
| 2014/0303434 A1 | 10/2014 | Farritor et al. |
| 2014/0303643 A1 | 10/2014 | Ha et al. |
| 2014/0305995 A1 | 10/2014 | Shelton, IV et al. |
| 2014/0309659 A1 | 10/2014 | Roh et al. |
| 2014/0316436 A1 | 10/2014 | Bar et al. |
| 2014/0323803 A1 | 10/2014 | Hoffman et al. |
| 2014/0324070 A1 | 10/2014 | Min et al. |
| 2014/0330288 A1 | 11/2014 | Date et al. |
| 2014/0364720 A1 | 12/2014 | Darrow et al. |
| 2014/0371577 A1 | 12/2014 | Maillet et al. |
| 2015/0039034 A1 | 2/2015 | Frankel et al. |
| 2015/0085970 A1 | 3/2015 | Bouhnik et al. |
| 2015/0146847 A1 | 5/2015 | Liu |
| 2015/0150524 A1 | 6/2015 | Yorkston et al. |
| 2015/0196261 A1 | 7/2015 | Funk |
| 2015/0213633 A1 | 7/2015 | Chang et al. |
| 2015/0335480 A1 | 11/2015 | Alvarez et al. |
| 2015/0342647 A1 | 12/2015 | Frankel et al. |
| 2016/0005194 A1 | 1/2016 | Schretter et al. |
| 2016/0166329 A1 | 6/2016 | Langan et al. |
| 2016/0235480 A1 | 8/2016 | Scholl et al. |
| 2016/0249990 A1 | 9/2016 | Glozman et al. |
| 2016/0302871 A1 | 10/2016 | Gregerson et al. |
| 2016/0320322 A1 | 11/2016 | Suzuki |
| 2016/0331335 A1 | 11/2016 | Gregerson et al. |
| 2017/0135770 A1 | 5/2017 | Scholl et al. |
| 2017/0143284 A1 | 5/2017 | Sehnert et al. |
| 2017/0143426 A1 | 5/2017 | Isaacs et al. |
| 2017/0156816 A1 | 6/2017 | Ibrahim |
| 2017/0202629 A1 | 7/2017 | Maillet et al. |
| 2017/0212723 A1 | 7/2017 | Atarot et al. |
| 2017/0215825 A1 | 8/2017 | Johnson et al. |
| 2017/0215826 A1 | 8/2017 | Johnson et al. |
| 2017/0215827 A1 | 8/2017 | Johnson et al. |
| 2017/0231710 A1 | 8/2017 | Scholl et al. |
| 2017/0258426 A1 | 9/2017 | Risher-Kelly et al. |
| 2017/0273748 A1 | 9/2017 | Hourtash et al. |
| 2017/0296277 A1 | 10/2017 | Hourtash et al. |
| 2017/0360493 A1 | 12/2017 | Zucher et al. |

* cited by examiner

STABILIZER WHEEL ASSEMBLY AND METHODS OF USE

CROSS REFERENCE TO RELATED APPLICATIONS

This application is a continuation of U.S. patent application Ser. No. 15/681,838 filed on Aug. 21, 2017 which is a continuation of U.S. patent application Ser. No. 14/881,291, filed on Oct. 13, 2015 (published as U.S. Patent Publication No. 2017-0101118), the contents of which is hereby incorporated by reference in its entirety for all purposes.

FIELD OF THE INVENTION

Embodiments are directed to a stabilizer wheel assembly and, more particularly, a stabilizer wheel assembly that may assist in stabilizing a medical device during a medical procedure.

BACKGROUND

Various medical devices may need to be stabilized before a medical procedure. However, most flooring may not be flat throughout the entire surface area. Often there may be high and low areas within flooring that may prevent a medical device from remaining stable. A stabilized medical device may be essential for many medical procedures. Even the slightest movement of the medical device may lead to catastrophic harm of a patient. Conventionally, medical personnel may place stops and/or wedges to help stabilize the medical device. This manual process, even if done correctly, may allow movement of the medical device during a medical procedure. The success of a medical procedure may largely depend on the stability of the medical device.

Consequently, there is a need for a stabilizer wheel assembly that may be used to stabilize a medical device. The ability to perform a medical procedure on a patient with a stable device may greatly diminish the possibility of harming a patient during the medical procedure. The application of a stabilizer wheel assembly and the techniques used with the stabilizer wheel assembly may enhance the overall medical procedure and the results of the procedure.

SUMMARY

An embodiment may include a medical device, wherein the medical device may comprise a body; and a plurality of stabilizer wheel assemblies coupled to the body, wherein the stabilizer wheel assemblies each comprise a motor assembly and a stabilization leg, wherein the motor assembly is configured to drive the stabilization leg onto a contact surface to stabilize the body.

Another embodiment may include a method of stabilizing a medical device, wherein the method may comprise positioning the medical device for a medical procedure; activating a plurality of stabilizer wheel assemblies of the medical device to lower a stabilization leg from each of the stabilizer wheel assemblies; and driving the stabilization leg of each of the stabilizer wheel assemblies onto a contact surface.

BRIEF DESCRIPTION OF THE DRAWINGS

For a detailed description of the preferred embodiments of the invention, reference will now be made to the accompanying drawings in which.

DETAILED DESCRIPTION

Embodiments relate generally to a stabilizer wheel assembly for use with medical devices. More particularly, embodiments relate to a motor assembly and stabilizing leg assembly mounted to a caster, which may be used to stabilize medical devices. A stabilizer wheel assembly may comprise a caster, a stem, a motor assembly, a bumper, and a stabilizing leg assembly. In embodiments, a medical device may have a plurality of stabilizer wheel assemblies. The stabilizer wheel assemblies may allow personnel to maneuver medical devices to a medical procedure with ease. The medical devices may then be positioned to help facilitate the medical procedure. In many cases, the floor upon which the medical devices may be disposed may be uneven. This may lead to sudden movement of medical devices during a medical procedure. The stabilizer wheel assembly may be used to stabilize medical devices and prevent sudden movements. In embodiments a stabilizing leg assembly and motor assembly may be used to drive a stabilization leg onto a contact surface. The stabilization leg may stabilize the medical device and help prevent sudden movements of the medical device.

Figure 1:
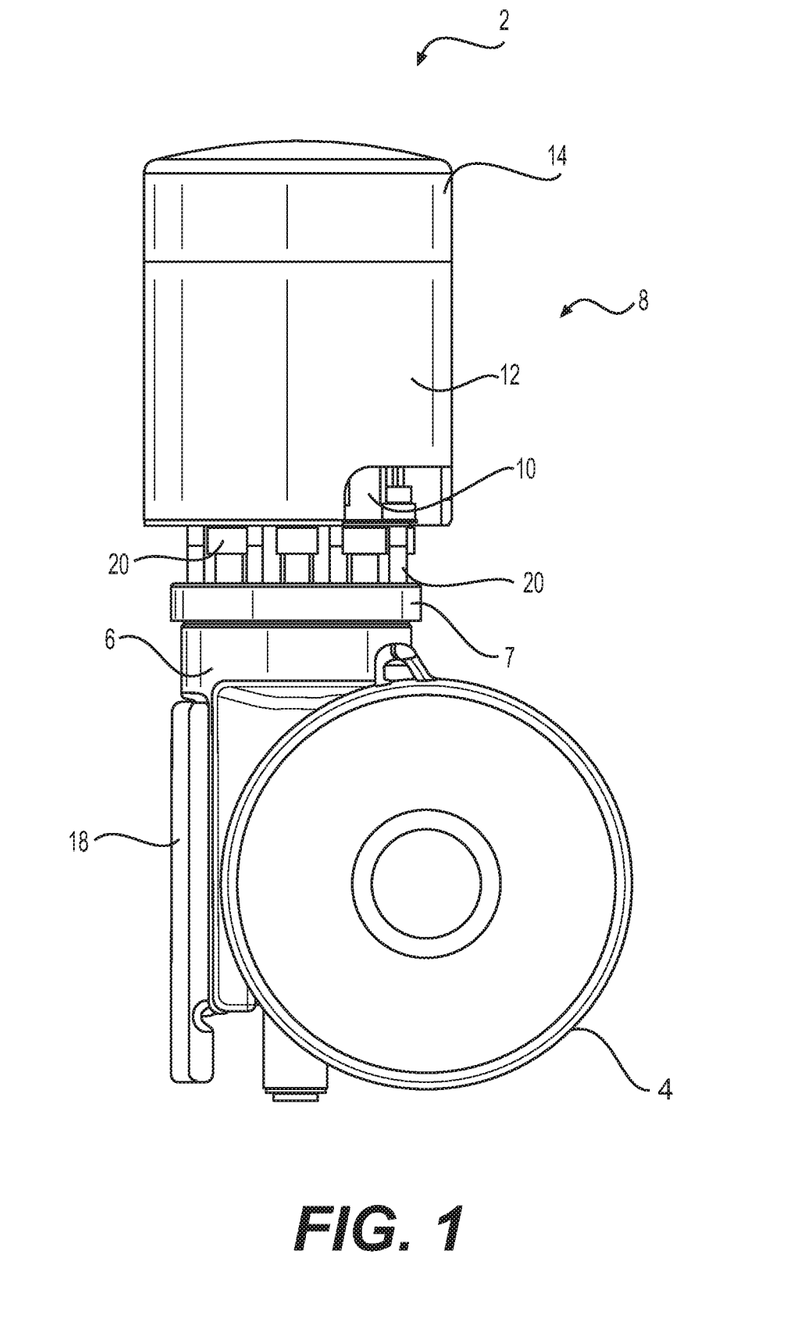
FIG. 1 illustrates an embodiment of a stabilizer wheel assembly.

FIG. 1 illustrates an embodiment of a stabilizer wheel assembly 2. Stabilizer wheel assembly 2 may comprise a caster 4, a stem 6, a motor assembly 8, attachment means 20, and a bumper 18. Caster 4 may be a structure upon which the rest of stabilizer wheel assembly 2 may be disposed. In embodiments, caster 4 may comprise a single, double, and/or compound wheels. Caster 4 may be any type of rigid, swivel, industrial, and/or braking and locking wheels. Caster 4 may comprise any material suitable for supporting and facilitating movement of a medical device. Suitable material may be, but is not limited to, rubber, plastic, nylon, aluminum, stainless steel, and/or any combination thereof. Additionally, caster 4 may be of any suitable diameter and width. A suitable diameter may be about one inch to about six inches, about two inches to about four inches, or about three inches to about six inches. A suitable width may be about a quarter inch to about two inches, about half an inch to about an inch, or about an inch to about two inches. In embodiments, caster 4 may rotate three hundred and sixty degrees around stem 6. Stem 6 may provide an additional structure which other components of stabilizer wheel assembly 2 may be disposed.

As illustrated in FIG. 1, stem 6 may be a structure in which caster 4, motor assembly 8, and bumper 18 are disposed. In embodiments, stem 6 may be a hollow tube with at least one flanged surface 7, best illustrated in FIG. 2. Referring to FIG. 1, caster 4 may attach to stem 6 through a tapered roller bearing and a coaxial roller bearing. A retaining ring captures caster 4 and prevents the caster housing from falling off the stem. Additionally, caster 4 may be disposed on stem 6 at any suitable location. In embodiments, caster 4 may be disposed about an edge and/or about the bottom of stem 6. Stem 6 may further house stabilizing leg assembly 22, as disclosed below. In embodiments, stem 6 may be made of any suitable material in which to support a medical device. Suitable material may be, but is not limited to, rubber, plastic, nylon, aluminum, stainless steel, and/or any combination thereof. Stem 6 may be any suitable length to support stabilizer wheel assembly 2. A suitable length may be about one inch to about six inches, about two inches to about four inches, or about three inches to about five inches. Additionally, stem 6 may have any suitable inside diameter in which to dispose stabilizing leg assembly 22. A suitable diameter may be about half an inch to about two inches, about three quarters of an inch to about an inch and a half, or about one inch to about two inches. Stabilizing leg assembly 22 may be powered by motor assembly 8. In embodiments, motor assembly 8 may be disposed upon stem 6.

Figure 2:
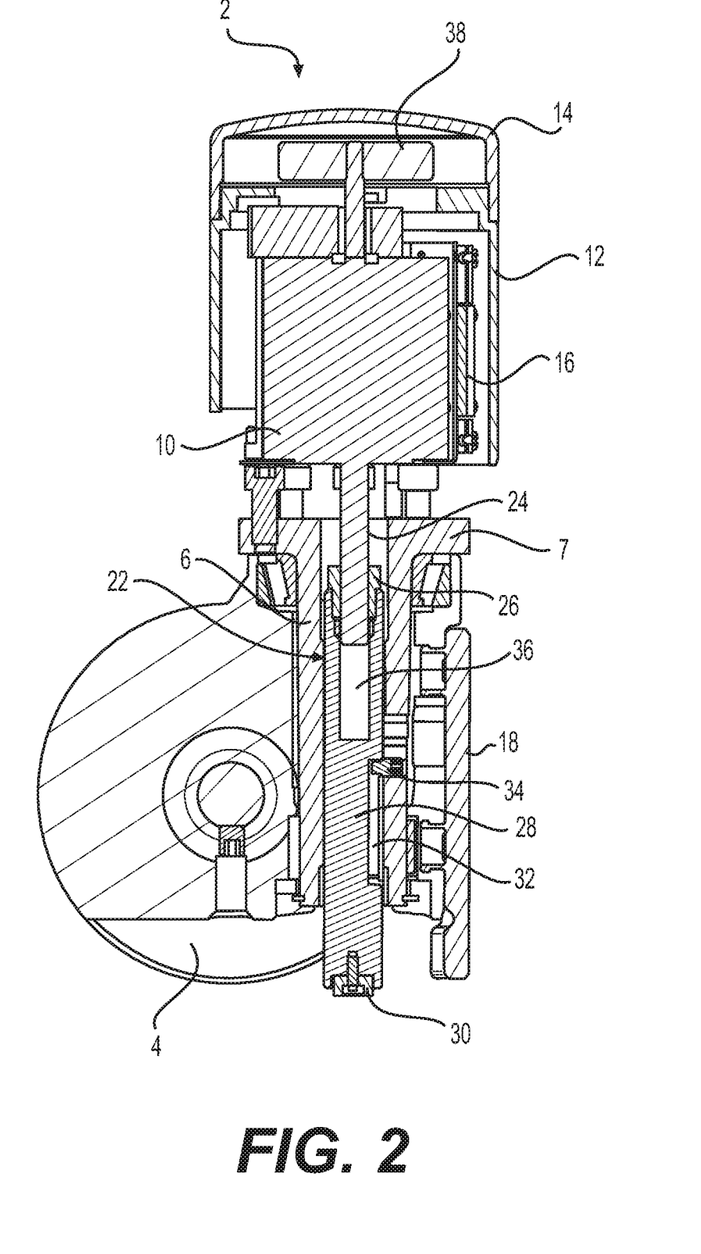
FIG. 2 illustrates a cutaway view of an embodiment of a stabilizer wheel assembly.
Figure 3:
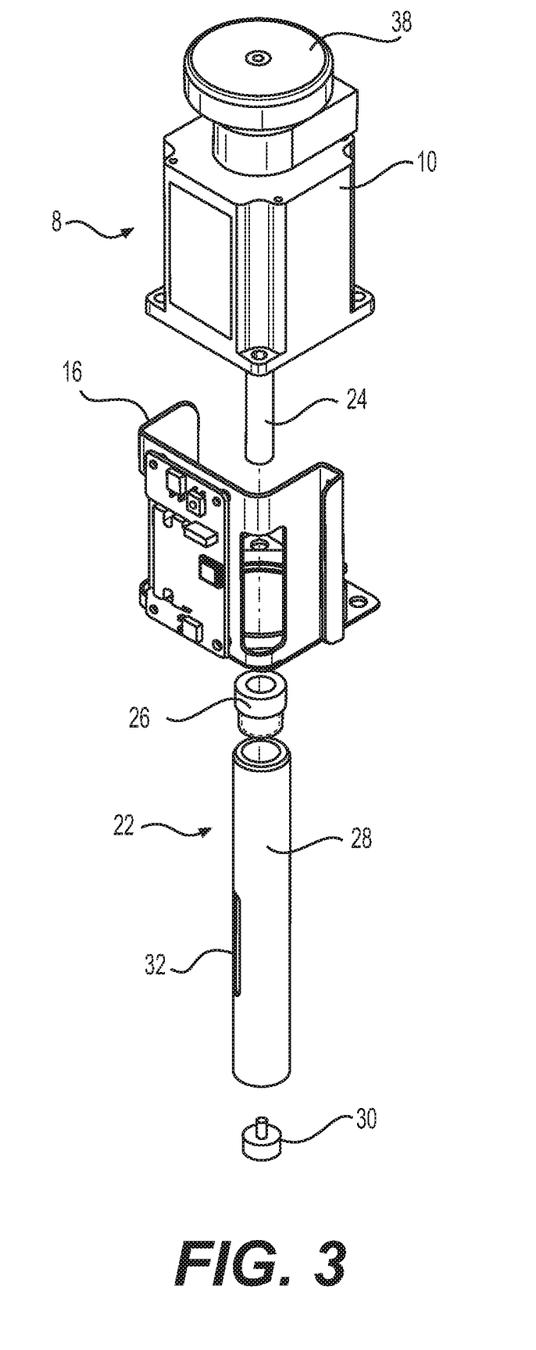
FIG. 3 illustrates an embodiment of a motor and a stabilizing leg assembly.

Referring to FIG. 3, motor assembly 8 may be disposed about the top of stem 6. Additionally, motor assembly 8 may be disposed upon stem 6 at any suitable location. In embodiments, motor assembly may be disposed about an edge and/or along the bottom of stem 6. Motor assembly 8 may attach to stem 6 by any suitable means. Suitable means may be, but are not limited to, nuts and bolts, screws, adhesive, and/or any combination thereof. As illustrated in FIGS. 1-3, motor assembly 8 may comprise a motor 10, a motor cover 12, a motor cap 14, and a motor bracket 16. Motor 10 may be a structure upon which motor cover 12, motor cap 14, and motor bracket 16 may be disposed. Additionally, motor 10 may attach about the top and/or about and edge of stem 6. In embodiments, motor 10 may be any type of suitable motor 10. A suitable motor 10 may be, but is not limited to, a permanent magnet stepper, a hybrid synchronous stepper, a variable reluctance stepper, a lavet type stepping motor, a brushed servo motor, and/or a brushless servo motor. Additionally, motor 10 may comprise a unipolar or bipolar stepper motor. In embodiments, motor 10 may attach to a motor bracket 16. Attachment means 20, as illustrated in FIGS. 1-3, may attach motor 10, motor bracket 16, and motor assembly 8 to stem 6. Attachment means 20 may be, but are not limited to, nuts and bolts, screws, press fittings, adhesive, and/or any combination thereof. In embodiments, attachment means 20 may further connect motor cover 12 to stem 6. There may be a plurality of attachment means 20 disposed about the top of stem 6.

Motor bracket 16, as illustrated in FIGS. 2 and 3, may be used to stabilize motor 10 and may protect motor 10 from outside forces. In embodiments, motor bracket 16 may comprise any suitable material to firmly hold and protect motor 10. Suitable material may be, but is not limited to, rubber, plastic, nylon, aluminum, stainless steel, and/or any combination thereof. Additionally, best illustrated in FIG. 3, motor bracket 16 may be used as an attachment point for communication circuitry, which may allow motor 10 to communicate with robot system 42 (discussed below on FIG. 6). In embodiments, motor 10 and motor bracket 16 may attach to stem 6 through attachment means 20. Motor bracket 16 may be disposed about any suitable location of motor 10. Specifically, motor bracket 16 may be disposed below, above, or about a side of motor 10. In embodiments, motor bracket 16 may be disposed between stem 6 and motor 10, which may secure motor bracket 16 in place. Motor bracket 16 may attach to stem 6 and/or motor 10 by any suitable means. Suitable means may be, but are not limited to, nuts and bolts, screws, adhesive, press fittings, and/or any combination thereof. In embodiments, motor bracket 16 and motor 10 may be enclosed by motor cover 12 and motor cap 14.

As illustrated in FIGS. 1 and 2, motor cover 12 and motor cap 14 may protect motor 10 from foreign objects and outside forces. Both motor cover 12 and motor cap 14 may comprise any suitable material which may protect motor 10 from foreign objects and outside forces. Suitable material may be, but is not limited to, rubber, plastic, nylon, aluminum, stainless steel, and/or any combination thereof. In embodiments, motor cap 14 may attach to motor cover 12 by any suitable means. Suitable means may be, but are not limited to, snap fittings, threaded fitting, adhesive, nuts and bolts, screws, O-rings, and/or any combination thereof. Motor cover 12 may be any suitable shape. A suitable shape may be, but is not limited to, circular, triangular, square, rectangular, polyhedral, and/or any combination thereof. Best illustrated in FIG. 4, motor cover 12 may be disposed at the top of motor 10. Additionally, motor cover 10 may be disposed below or at about any edge of motor 10. In embodiments, motor cover 10 may partially enclose components of motor assembly 8. Motor cap 14 may be disposed on top of motor cover 12 and/or motor 10, which may partially enclose components of motor assembly 8. In embodiments, motor cap 14 may attach to motor cover 12 or motor 10 by any suitable means. Suitable means may be, but are not limited to, nuts and bolts, screws, adhesive, press fitting, O-ring, and/or any combination thereof. Motor cover 12 may be any suitable shape. A suitable shape may be, but is not limited to, circular, triangular, square, rectangular, polyhedral, and/or any combination thereof. Motor cover 12 and motor cap 14 may protect motor assembly 8. Stabilizer wheel assembly may further be protected from outside forces by bumper 18.

Bumper 18, as illustrated in FIGS. 1 and 2, may protect stem 6 from foreign objects, outside forces, and may prevent cables and/or other cords from going under stem 6. Bumper 18 may be made of any suitable material to absorb impacts from foreign objects and prevent objects from sliding under stem 6. Suitable material may be, but is not limited to, rubber, plastic, nylon, polyurethane, and/or any combination thereof. In embodiments bumper 18 may snap fit into the caster or by any suitable means. Suitable means may be, but are not limited to, snap fittings, adhesive, nuts and bolts, screws, and/or any combination thereof. Bumper 18 may be any suitable shape. A suitable shape may be, but is not limited to, circular, triangular, square, rectangular, polyhedral, and/or any combination thereof. In embodiments, bumper 18 may be disposed opposite casters 4. Additionally, bumper 18 may be disposed about any edge and a plurality of bumpers 18 may be disposed along any number of edges of stem 6. Any item under stem 6 may prevent stabilizing leg assembly 22 from operating correctly, which may prevent stabilization of a medical device. Removing objects from stem 6 may allow for stabilizing leg assembly 22 to firmly stabilize a medical device. Bumper 18 may be any suitable length in which to prevent objects from moving below stem 6. In embodiments, best illustrated in FIG. 1, bumper 18 may almost touch the same contact surface as caster 4. This additional length may facilitate in pushing and/or removing cables and other objects from the path of caster 4 and stem 6. Removing objects from beneath stabilizing leg assembly 22 may allow properly stabilize medical robot system 42, discussed below.

As illustrated in FIGS. 2 and 3, stabilizing leg assembly 22 may be used to stabilize a medical device. Stabilizing leg assembly 22 may comprise a lead screw 24, a nut 26, a stabilizing leg 28, a foot 30, a channel 32, and a set screw 34. To prevent failure of stabilizing leg assembly 22 under weight of a medical device, stabilizing leg assembly may be made of any suitable material to support the weight of the medical device. Suitable material may be, but is not limited to, rubber, plastic, nylon, aluminum, stainless steel, and/or any combination thereof. In embodiments, lead screw 24 may be directly disposed within motor 10. Lead screw 24 may be disposed below and/or within motor 10. Lead screw 24 may attach to motor 10 by any suitable means. Suitable means may be, but are not limited to, nuts and bolts, screws, adhesive, press fittings, and/or any combination thereof. In embodiments, lead screw 24 may operate as a transmission shaft, which may rotate in any direction, distributing rotational force to an attached device. Additionally, lead screw 24 may rotate as fast and/or as slow as motor 10 may allow. Rotation of lead screw 24 may remove stabilizing leg 28 from a contact surface and may dispose stabilizing leg 28 onto the contact surface. In embodiments, lead screw 24 may comprise low pitch threading. Low pitch threading may require more revolutions of lead screw 24 in order to move stabilizing leg 28 up and/or down. Low pitch threading as well as high friction or inefficient force transmission may prevent lead screw 24 from moving and/or rotating under the weight of a medical device, which may prevent stabilizing leg 28 from collapsing into stabilizer wheel assembly 2. The rotational force, for creating up and down movement of stabilizing leg 28, may be transferred from lead screw 24 to stabilizing leg 28 through nut 26. Nut 26 may be disposed upon lead screw 24 and stabilizing leg 28.

As illustrated in FIGS. 2 and 3, nut 26 may attach to stabilizing leg 28 by any suitable means. Suitable means may be, but are not limited to, weld, adhesive, forming, nuts and bolts, screws, and/or any combination thereof. Nut 26 may be disposed at an end of stabilizing leg 28 opposite foot 30 and closest to motor 10. In embodiments, the rotation of lead screw 24 may move nut 26, and in turn stabilizing leg 28, up and down. As nut 26 and stabilizing leg 28 traverse lead screw 24, lead screw 24 may enter into a pocket 36 of stabilizing leg 28, best illustrated in FIG. 2. Pocket 36 may allow stabilizing leg 28 and nut 26 to traverse lead screw 24 without binding and/or collapsing lead screw 24. In embodiments, pocket 36 may be a hollow section within stabilizing leg 28. Pocket 36 may traverse the length of stabilizing leg 28 and/or be located at an end of stabilizing leg 28 opposite foot 30. Pocket 36 may allow for stabilizing leg 28 to rotate, be risen, and/or lowered without harming stabilizing leg 28. In embodiments, to prevent stabilizing leg 28 from rotating with lead screw 24, a channel 32 and set screw 34 may be used to prevent rotational motion of stabilizing leg 28.

Figure 4:
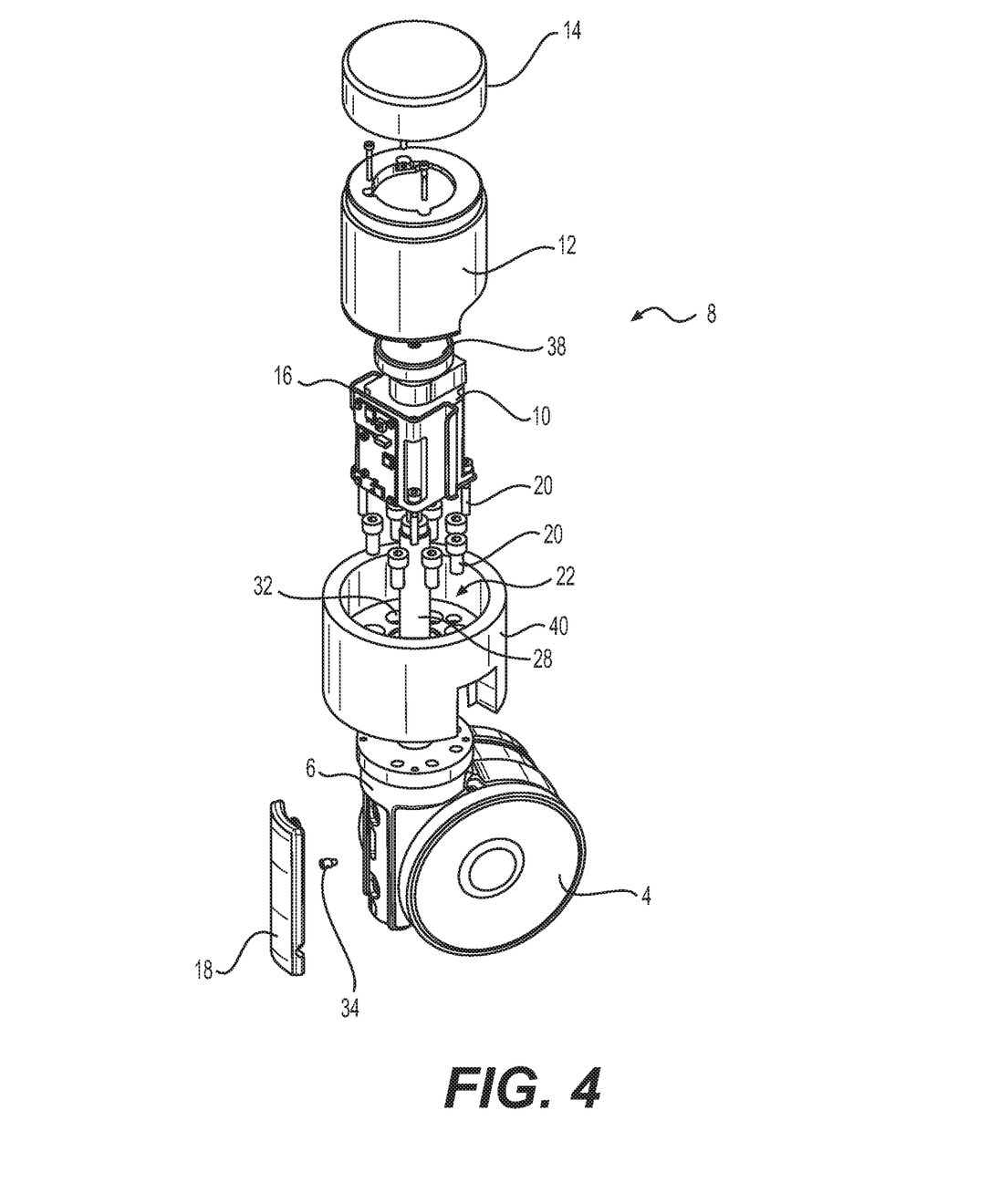
FIG. 4 illustrates an exploded view of an embodiment of a stabilizer wheel assembly.

Best illustrated in FIGS. 2 and 3, channel 32 may be a vertical cut-out along stabilizing leg 28. Channel 32 may be disposed along any edge of stabilizing leg 28. Additionally, channel 32 may be disposed on an edge of stabilizing leg 28 closest to bumper 18 and opposite caster 4. In embodiments, channel 32 may run the length of movement allowed by stabilizer motor 10. In additional embodiments, channel 32 may run the entire length of stabilizing leg 28. Referring to FIGS. 2 and 4, a set screw 34 may protrude through stem 6 and into channel 32. In embodiments, set screw 34 may be disposed along any edge of stem 6. Specifically, set screw 34 may be disposed at an edge opposite caster 4 and closest to bumper 18. Set screw 34 may attach to stem 6 by any suitable means, suitable means may be, but are not limited to, a snap fitting, threaded fitting, nuts and bolts, and/or any combination thereof. Protruding into channel 32 from stem 6, set screw 34 may prevent the rotational movement, in any direction, of stabilizing leg 28. This may allow stabilizing leg 28 to move up and/or down and not rotate with lead screw 24. In embodiments, stabilizing leg 28 may contact any surface. A foot 30 may act as a buffer between stabilizing leg 28 and the contact surface.

Foot 30, as illustrated in FIGS. 2 and 3 may act as a medium between stabilizing leg 28 and a contact surface. Foot 30 may comprise any suitable material in which to prevent damage and movement of stabilizing leg 28. Suitable material may be, but is not limited to, rubber, plastic, nylon, polyurethane, and/or any combination thereof. In embodiments, foot 30 may be any suitable shape. A suitable shape may be, but is not limited to circular, triangular, oval, square, rectangular, polyhedral, and/or any combination thereof. Additionally, foot 30 may attach to stabilizing leg 28 by any suitable means. Suitable means may be, but are not limited to, nuts and bolts, screws, adhesive, press fitting, and/or any combination thereof. Foot 30 may be disposed at an end of stabilizing leg 28 opposite nut 26 and farthest away from motor 10. In embodiments, foot 30 may increase the friction between stabilizing leg 28 and a contact surface, which may further help prevent movement of stabilizing leg 28. In embodiments, the force exerted upon a contact surface by stabilizing leg 28 and foot 30 may be controlled by medical robot system 42.

Figure 5:
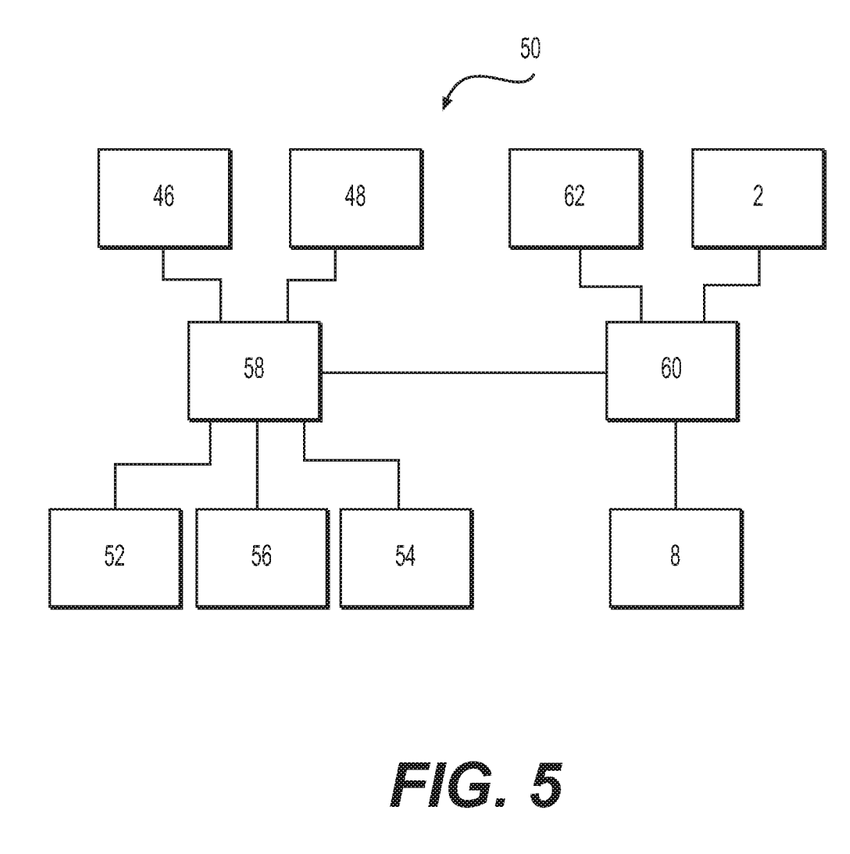
FIG. 5 illustrates an embodiment of a computer infrastructure.

FIG. 5 illustrates a schematic of software architecture 50 which may be used within medical robot system 42 to communicate with stabilizer wheel assembly 2. Software architecture 50 may be used to lower and raise stabilizing leg 28. Additionally, software architecture 50 may allow an operator to manipulate medical robot system 42 based upon commands given from an operator. In examples, operator commands may comprise Picture Archival and Communication Systems (PACS) 52, USB Devices 90, and commands from a wireless device 56. These operator commands may be received and transferred throughout medical robot system 42 by a computer processor 58. Computer processor 58 may be able to receive all commands and manipulate medical robot system 42 accordingly. In examples, computer processor 58 may be able to control and identify the location of individual parts that comprise medical robot system 42. Communicating with tool assembly 46 and display assembly 48, discussed below, computer processor 58 may be able to assist medical personnel during a medical procedure. Additionally, computer processor 58 may be able to use commands from display assembly 48 to alter the positions of tool assembly 46. Computer processor 58 may use firmware 60 to issue commands and process signals. Firmware 60 may comprise commands that are hardwired to medical robot system 42. For example, computer processor 58 may communicate with stabilizer wheel assembly 2, and platform interface 62. Platform interface 62 may be a series of hardwired button commands that directly control medical robot system 42. Button commands are not limited to but may comprise functions that may move lower and rise stabilization legs 28. Additionally, computer processor 92 may process and distribute all operator commends from display assembly 48 to lower and rise stabilization legs 28.

To stabilize a medical device, computer processor 58 disposed within the medical robot system 42 may be used to communicate with stabilizer wheel assembly 2 to exert a predetermined amount of force through stabilizing leg 28 to a contact surface. Motor 10 may use firmware 60 to interface with computer processor 58 disposed within medical robot system 42. Suitable firmware 60 may be, but is not limited to I2C and SPI. In embodiments, disposing stabilizing leg 28 onto a contact surface may be broken down into two states, a ground state and a lifting state. These states may help stabilize the medical device in a controlled manner.

In embodiments, the ground state may dispose stabilizing leg 28 and foot 30 onto a contact surface without applying force upon the contact surface. This may be accomplished by driving motor 10 at a low current, about 0.01 Amps to about 1.2 Amps, and monitoring for two encoder-based stop conditions. The first stop condition may be measuring instantaneous speed along an encoder frequency. A peak width of an encoder channel may be chosen as a proxy for frequency as the base line. With low torque, a certain empirically determined peak width may be encountered while stabilizing leg 28 may be moving with no resistance. Resistance may produce a consecutive number of peak widths that may be higher than the original base line, which may satisfy the first stop condition. The second stop condition may comprise of reading a moving average of peak counts at 100 ms, which may simply be a measurement of displacement over time. If the value falls below a quarter percent of the empirically determined "no load" average displacement, the second stop condition is satisfied. Both conditions may be satisfied simultaneously and/or separately, but both conditions must be met to complete the ground state. Satisfying the ground state, the second lift state may then begin. During the lift state, a current of about 2.5 Amps to about 4 Amps may be applied to the motor. The second lift state may only measure the encoder count of lead screw 24 revolutions. Meeting a predetermined count or a timeout condition, the second lift state may end. The second lifting state may be based on a prescribed displacement of stabilizing leg 28 and not force and/or torque. Additionally, the onboard computer, disposed on the medical device, may use states to retract stabilizing leg 28 from a contact surface. The system just drives the stabilizers up into the caster. In embodiments, stabilizing leg 28 may move manually upon activation of a manual override switch 38.

As illustrated in FIGS. 2 and 3, a manual override switch 38 may be disposed about the top and/or about an edge of motor 10. In embodiments, override switch 38 may attach to lead screw 24. In the event medical robot system 42 loses power, medical personnel may need to retract stabilizing leg 28 and foot 30 from the contact surface. A loss of power may prevent motor 10 from retracting stabilizing leg 28. Manual override switch 38 may be manually rotated to retract and/or lower stabilizing leg 28. In embodiments, manual override switch 38 may be made of any suitable material to facilitate rotation of lead screw 24. Suitable material may be, but is not limited to, rubber, plastic, nylon, aluminum, stainless steel, and/or any combination thereof. Manual override switch 38 may be any suitable shape. A suitable shape may be, but is not limited to circular, oval, square, triangular, rectangular, polyhedral, and/or any combination thereof Rotation of manual override switch 38 may rotate lead screw 24 and in turn move stabilizing leg 28 up and down. This may allow medical personnel to move the medical device without power, even when stabilizing leg 28 is activated. Additionally, manual override switch 38 may be rotated in an opposite direction, which may lower stabilizing leg 28 on to a contact surface. In embodiments, manual override switch 38 may be accessed by removing motor cap 14. Motor assembly 2 may be disposed at any suitable location within medical robot device 42, which may allow access to manual override switch 38.

As illustrated in FIG. 4, a medical device attachment 40 may be attach to stabilizer wheel assembly 2 between stem 6 and motor assembly 8 through attachment devices 20. Medical device attachment 40 may transfer the weight of a medical device to stabilizer wheel assembly 2. In embodiments, medical device attachment 40 may also help protect stabilizer wheel assembly 2 from foreign objects and outside forces. Medical device attachment 40 may be made of any suitable material to structurally support the medical device and protect stabilizer wheel assembly 2 form foreign objects and outside forces. Suitable material may be, but is not limited to, rubber, plastic, nylon, aluminum, stainless steel, and/or any combination thereof. In embodiments, medical device attachment 40 may have any suitable geometry in which to properly attach to a medical device. A suitable geometry may be circular, square, triangular, polyhedral, oval, and/or any combination thereof. Medical device attachment 40 may be used to attach any number of stabilizer wheel assemblies to medical robot system 42.

Figure 6:
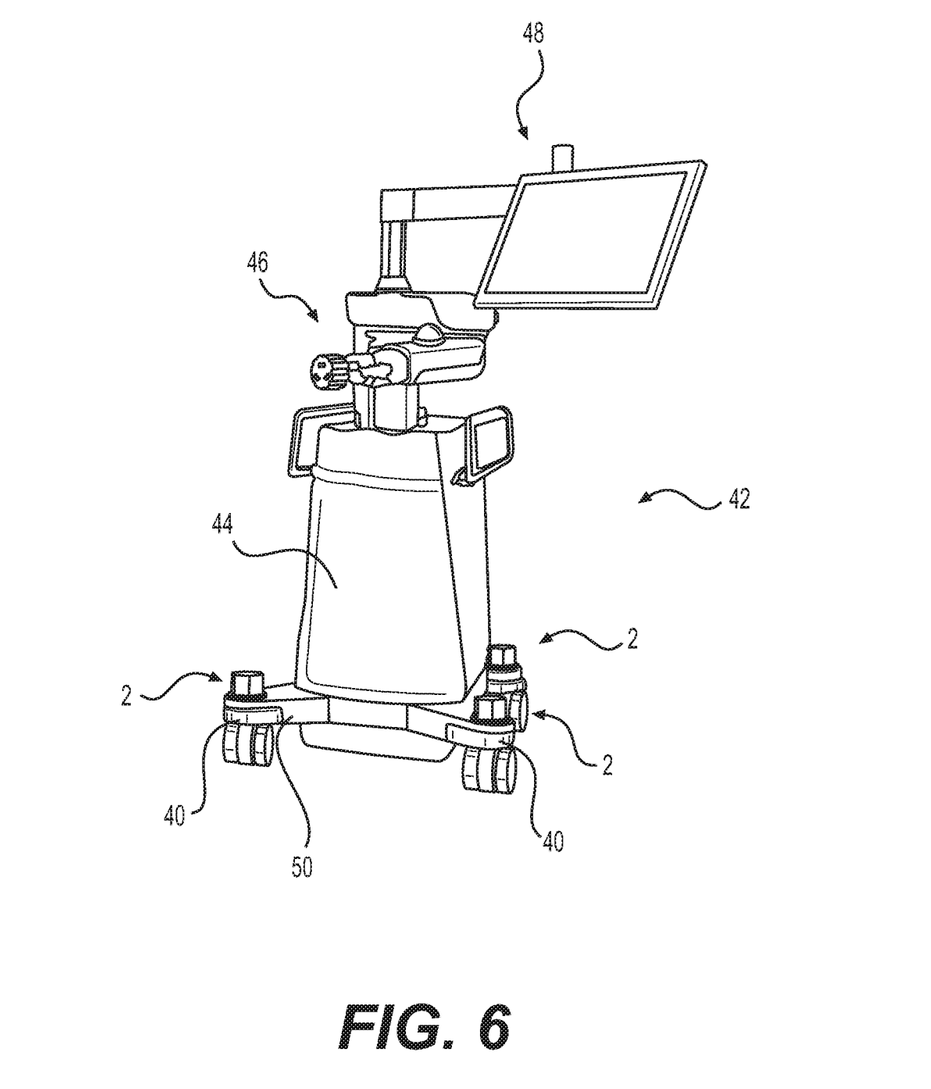
FIG. 6 illustrates and embodiment of a medical robot system.

Referring now to FIG. 6, a medical robot system 42 is illustrated in accordance with embodiments of the present invention. In the illustrated embodiment, the medical robot system comprises body 44, tool assembly 46, display assembly 48, and base 50. In embodiments, base 50 may provide a structure upon which stabilizer wheel assembly 2 and body 44 may be disposed. Stabilizer wheel assembly 2 may attach to base 50 through medical device attachments 40. Medical device attachments 40 may connect to base 50 by any suitable means. Suitable means may be, but are not limited to, nuts and bolts, screws, adhesive, press fittings, and/or any combination thereof. Additionally, there may be any suitable number of stabilizer wheel assemblies 2 to support and provide movement to base 50. In the illustrated, four stabilizer wheel assemblies 2 are shown arranged around the periphery of base. In embodiments, body 44 may be disposed on top of base 50. Body 44 may provide structure to medical robot system 42. Additionally, tool assembly 46 and display assembly 48 may be disposed at any suitable location on body 44. Tool assembly 46 may be disposed on top, about an edge, or about a side of body 44. Specifically, tool assembly 46 maybe disposed about the center of the top of base 44. Without limitation, tool assembly 46 may be configured to hold a surgical tool in a medical procedure. In embodiments, display assembly 48 may be disposed on top, about an edge, or about a side of body 44 or tool assembly 46. Specifically, display assembly 48 maybe disposed on top of tool assembly 46. In embodiments, body 4 may further house electronics, not illustrated, which may control medical robot system 42. It should be understood that medical robot system 42 illustrated on FIG. 6 is merely illustrative and the stabilizer wheel assemblies 2 may be used for stabilization of any of a variety of different medical robot systems.

To perform a medical procedure, medical robot system 42 may be moved from storage to a medical procedure room using stabilizer wheel assemblies 2. Stabilizer wheel assemblies 2 may allow medical personnel to maneuver medical robot system 42 around corners, through doors, through hallways, and elevators. Additionally, stabilizer wheel assemblies 2 may move medical robot system 42 in any direction and may allow for medical robot system 42 to rotate. After being positioned for a medical procedure, stabilizer wheel assemblies 2 may be activated using on board computers and circuitry housed in body 44. Display assembly 48 may provide an interface in which medical personnel may activate and control stabilizer wheel assemblies 2. Stabilizing leg 28 may be disposed to contact the surface below stabilizer wheel assemblies 2. As described above, a designated amount of force may be applied through stabilizing leg 28 to the contact surface. Applying an equal amount of force at each stabilizer wheel assembly 2 may create a stable platform, which may prevent medical robot system 42 from moving during a medical procedure. When medical robot system 42 may need to be moved after being activated, medical personnel may retract stabilizing leg 28 from the contact surface using display assembly 48 and/or manual override switch 38. Medical robot system 42 may then be maneuvered to any location for storage and/or further use.

Although the present invention and its advantages have been described in detail, it should be understood that various changes, substitutions and alterations may be made herein without departing from the spirit and scope of the invention as defined by the appended claims.

What is claimed is:

1. A method of stabilizing a medical robot system comprising the steps of:
    providing a medical robot system comprising:
        a body;
        a computer processor disposed within the body;
        a tool assembly attached to the body;
        a display assembly attached to the body;
        a base attached to the body; and
        at least one stabilizer wheel assembly disposed on the base,
        wherein each stabilizer wheel assembly comprises a motor and a stabilizer leg, and
        wherein each stabilizer wheel assembly comprises a foot attached to an end of the corresponding stabilization leg opposite a nut,
    receiving one or more commands from a platform interface to move each stabilizer leg by controlling each motor
    wherein each stabilizer wheel assembly further comprises a bumper.

2. The method of claim 1, wherein the steps further include driving each stabilization leg into a contact surface until each stabilization leg exerts a predetermined force on the contact surface.

3. The method of claim 2, wherein each stabilizer wheel assembly further comprises a caster.

4. The method of claim 3, wherein each stabilizer wheel assembly further comprises a stem, wherein the corresponding caster rotates three hundred and sixty degrees around each stem.

5. The method of claim 4, wherein each motor is connected to a top of the corresponding stem.

6. The method of claim 5, wherein the steps further include extending each stabilization leg through the corresponding caster to the contact surface.

7. The method of claim 1, wherein each stabilizer wheel assembly further comprises a motor cover that encloses each motor, a motor cap disposed on top of each motor, and a motor bracket that supports each motor.

8. The method of claim 1, wherein each foot increases the friction between the corresponding stabilization leg and a contact surface.

9. The method of claim 8, wherein each stabilizer wheel assembly further comprises a caster and a set screw is disposed on a side of the caster.

10. The method of claim 9, wherein the steps further include securing each stabilizer wheel assembly into a corresponding channel to prevent the corresponding stabilization leg from rotating.

11. A method of stabilizing a medical robot comprising the steps of:
    providing the medical robot comprising:
        a body;
        a stabilizer wheel assembly coupled to the body, wherein the stabilizer wheel assembly comprises a motor assembly and stabilization leg, wherein the motor assembly is configured to drive the stabilization leg onto a contact surface to stabilize the body; and
        a computer processor disposed within the body,
        wherein the stabilizer wheel assembly comprises a foot attached to an end of the corresponding stabilization leg opposite a nut
    receiving one or more commands from a platform interface to move each stabilizer leg by controlling each motor
        wherein each stabilizer wheel assembly further comprises a bumper.

12. The method of claim 11, wherein the steps further include driving the stabilization leg into the contact surface until the stabilization leg exerts a predetermined force on the contact surface.

13. The method of claim 12, wherein the stabilizer wheel assembly further comprises a caster.

14. The method of claim 13, wherein the stabilizer wheel assembly further comprises a stem, wherein the caster rotates three hundred and sixty degrees around the stem.

15. The method of claim 14, wherein the motor assembly is connected to a top of the stem.

16. The method of claim 15, further includes the step of extending the stabilization leg through the caster to the contact surface.

17. The method of claim 11, wherein the motor assembly further comprises a motor, a motor cover that encloses each motor, a motor cap disposed on top of each motor, and a motor bracket that supports each motor.

18. The method of claim 11, wherein the stabilizer wheel assembly comprises a foot attached to an end of the stabilization leg opposite a nut.

19. A method of stabilizing a medical robot system comprising the steps of:
    providing a medical robot system comprising:
        a body;
        a computer processor disposed within the body;
        a tool assembly attached to the body;
        a display assembly attached to the body;
        a base attached to the body; and
        at least one stabilizer wheel assembly disposed on the base,
        wherein each stabilizer wheel assembly comprises a motor and a stabilizer leg, an
    receiving one or more commands from a platform interface to move each stabilizer leg by controlling each motor
    wherein each stabilizer wheel assembly further comprises a bumper.

* * * * *